United States Patent
Nair et al.

(10) Patent No.: US 10,858,387 B2
(45) Date of Patent: Dec. 8, 2020

(54) PROCESS FOR THE PREPARATION OF DEOXYCHOLIC ACID

(71) Applicant: Glenmark Life Sciences Limited, Solapur (IN)

(72) Inventors: Ranjeet Nair, Mumbai (IN); Shekhar Bhaskar Bhirud, Mumbai (IN); Nandkumar Gaikwad, Navi Mumbai (IN); Sharad R. Gore, Kalyan West (IN); Rajendra C. Jagdhane, Pune (IN); Sandip Gadge, Pune (IN); Sukumar Sinha, Navi Mumbai (IN)

(73) Assignee: GLENMARK LIFE SCIENCES LIMITED, Solapur (IN)

( * ) Notice: Subject to any disclaimer, the term of this patent is extended or adjusted under 35 U.S.C. 154(b) by 0 days.

(21) Appl. No.: 16/615,990

(22) PCT Filed: May 21, 2018

(86) PCT No.: PCT/IB2018/053556
§ 371 (c)(1),
(2) Date: Nov. 22, 2019

(87) PCT Pub. No.: WO2018/215908
PCT Pub. Date: Nov. 29, 2018

(65) Prior Publication Data
US 2020/0140478 A1 May 7, 2020

(30) Foreign Application Priority Data

May 25, 2017 (IN) .............................. 201721018371

(51) Int. Cl.
*C07J 9/00* (2006.01)

(52) U.S. Cl.
CPC ..................................... *C07J 9/005* (2013.01)

(58) Field of Classification Search
CPC ........................................................ C07J 9/00
USPC ......................................................... 552/553
See application file for complete search history.

(56) References Cited

U.S. PATENT DOCUMENTS

| 2,697,105 A | 12/1954 | Baker et al. |
| 2013/0085125 A1 * | 4/2013 | Ganley .................... C07J 9/005 514/182 |

FOREIGN PATENT DOCUMENTS

| WO | 2012174229 A2 | 12/2012 |
| WO | 2014020024 A1 | 2/2014 |
| WO | PCT/IB2018/053556 | 10/2018 |

OTHER PUBLICATIONS

Haslewood et al., Biochem J, (1943), 37(1), p. 109-112.*

* cited by examiner

*Primary Examiner* — Yong L Chu
(74) *Attorney, Agent, or Firm* — Ryan, Mason & Lewis, LLP

(57) ABSTRACT

The present invention provides a process for preparation of deoxycholic acid or salt thereof; the process comprises the steps of reacting the compound of formula II to obtain a compound of formula III; the compound of formula III is converted to a compound of formula IV and the compound of formula IV is converted to deoxycholic acid. The present invention also provides a process for the purification of deoxycholic acid or salt thereof.

15 Claims, 1 Drawing Sheet

Glenmark Pharmaceuticals Limited                                      Figure 1
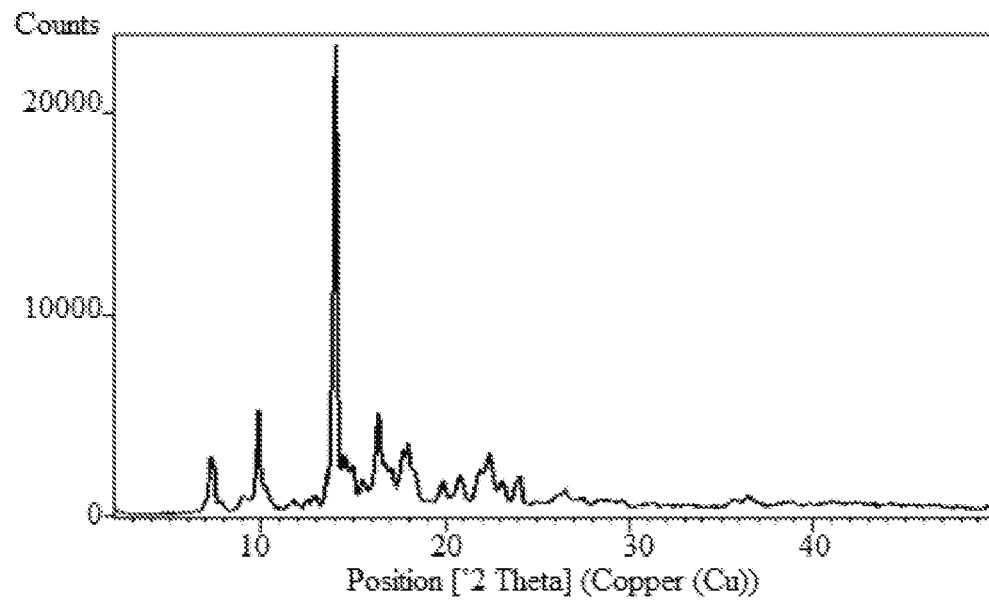
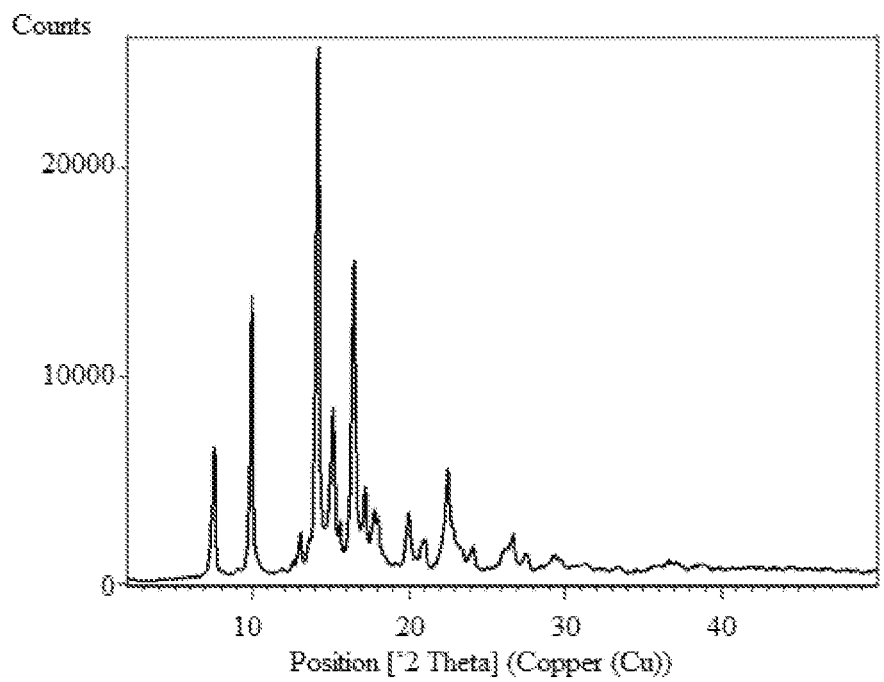
Glenmark Pharmaceuticals Limited                                      Figure 2

PROCESS FOR THE PREPARATION OF DEOXYCHOLIC ACID

PRIORITY

This application claims priority under 35 U.S.C. § 371 to International Application No. PCT/IB2018/053556, filed May 21, 2018 which claims the benefit of Indian Provisional Application No. 201721018371 filed May 25, 2017 and entitled "PROCESS FOR THE PREPARATION OF DEOXYCHOLIC ACID", the contents of which are incorporated herein by reference.

FIELD OF THE INVENTION

The present invention relates to a process for the preparation of deoxycholic acid, compound of formula I.

BACKGROUND OF THE INVENTION

Deoxycholic acid is chemically defined as 3α,12α-dihydroxy-5β-cholan-24-oic acid and is structurally represented in formula I.

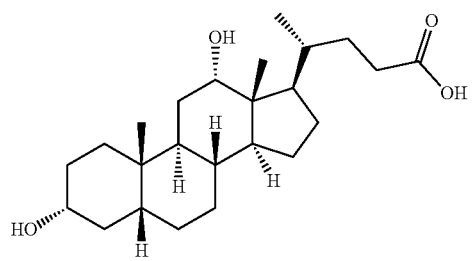

Formula I

Deoxycholic acid (KYBELLA™) is a cytolytic drug indicated for improvement in the appearance of moderate to severe convexity or fullness associated with submental fat in adults.

SUMMARY OF THE INVENTION

The present invention provides a process for the purification of deoxycholic acid or salt thereof, comprising the steps of:

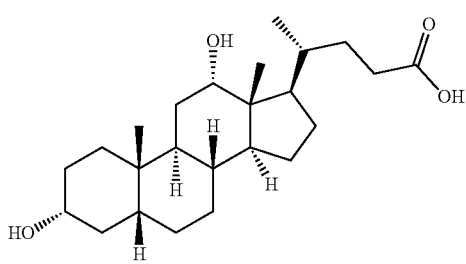

a) dissolving the crude deoxycholic acid or salt thereof in an ether solvent; and
b) isolating the pure deoxycholic acid or salt thereof by combining the solution obtained in (a) with a second solvent, followed by optional cooling.

BRIEF DESCRIPTION OF THE DRAWINGS

FIG. 1 is a characteristic XRPD of deoxycholic acid as obtained in Example 3 after tetrahydrofuran acetonitrile purification.

FIG. 2 is a characteristic XRPD of deoxycholic acid as obtained in Example 4.

DETAILED DESCRIPTION OF THE INVENTION

The present invention provides a process for the purification of deoxycholic acid or salt thereof, comprising the steps of:

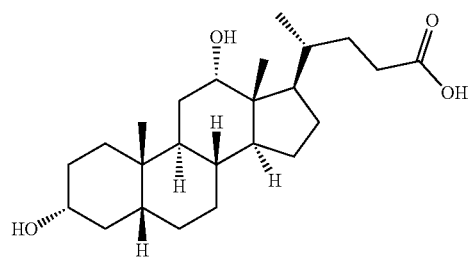

a) dissolving the crude deoxycholic acid or salt thereof in an ether solvent; and
b) isolating the pure deoxycholic acid or salt thereof by combining the solution obtained in (a) with a second solvent, followed by optional cooling.

The present invention provides a process for the purification of deoxycholic acid or salt thereof, comprising the steps of:

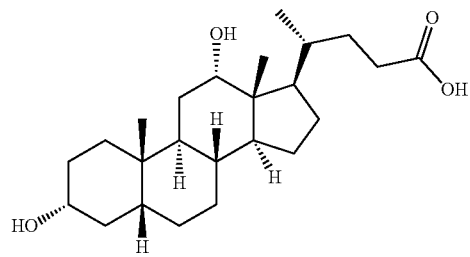

a) dissolving the crude deoxycholic acid or salt thereof in an ether solvent; and
b) isolating the pure deoxycholic acid or salt thereof by
   (i) cooling the solution obtained in (a); or
   (ii) removing the ether solvent from the solution obtained in (a); or
   (iii) combining the solution obtained in (a) with a second solvent followed by optional cooling.

The term crude deoxycholic acid refers to deoxycholic acid which is obtained by any method known in the art and may be isolated in a solid form or as a residue by removal of the solvent by evaporation or distillation from the reaction medium.

The term crude deoxycholic acid refers to deoxycholic acid with a chemical purity of about 50%-98% w/w as determined by HPLC.

In one embodiment, the term crude deoxycholic acid refers to deoxycholic acid with a chemical purity of about 98% as determined by HPLC.

In one embodiment in step a, the crude deoxycholic acid or salt thereof is dissolved in an ether solvent.

The ether solvent may be selected from the group consisting of diethyl ether, methyl tertiary butyl ether, diisopropyl ether, tetrahydrofuran, dioxane, and mixtures thereof.

The dissolution may be carried out at room temperature or at a temperature in the range of 50-100° C.

In one embodiment, in step b (i) the pure deoxycholic acid may be isolated by cooling the hot solution of deoxycholic acid in an ether solvent obtained in step a.

In one embodiment, the cooling may be carried out at a temperature in the range of −20° C. to 20° C.

In one embodiment, in step b (ii) the pure deoxycholic acid may be isolated by removing the ether solvent from the solution obtained in step a by solvent distillation, concentration, spray drying, fluid bed drying, lyophilization, flash drying, spin flash drying or thin-film drying.

In one embodiment, the pure deoxycholic acid may be isolated, by combining the solution obtained in (a) with a second solvent.

The second solvent may be selected such that on addition of the second solvent to the solution of deoxycholic acid in ether, the deoxycholic acid is precipitated out.

In one embodiment, the second solvent may be selected from the group consisting of nitrile, hydrocarbon, water and mixtures thereof.

The nitrile solvent may be selected from the group consisting of acetonitrile, propionitrile and the like.

The hydrocarbon solvent may be selected from aliphatic hydrocarbons like hexane, heptane, cyclohexane and the like or aromatic hydrocarbon like toluene, xylene.

In one embodiment, the addition of the second solvent may be carried out at room temperature.

In one embodiment, the addition of the second solvent may be carried out at a temperature in the range of 40-90° C.

In one embodiment, the addition of the second solvent may be carried out at a temperature in the range of 40-90° C. and the reaction mass thus obtained is then cooled to precipitate out the pure deoxycholic acid.

In one embodiment, cooling may be carried out at a temperature in the range of −20° C. to 20° C.

In one embodiment, the volume by volume ratio of second solvent to ether is in the range of 15:1 to 1:1.

In one embodiment, the volume by volume ratio of second solvent to ether is in the range of 9:1 to 2:1.

In one embodiment, present invention provides a process for deoxycholic acid or salt thereof, comprising the steps of:
a) dissolving the crude deoxycholic acid or salt thereof in an ether solvent; and
b) isolating the pure deoxycholic acid or salt thereof by combining the solution obtained in (a) with a nitrile solvent followed by optional cooling.

In one embodiment, the addition of nitrile may be carried out at a temperature in the range of 40-90° C. and the reaction mass is then cooled to precipitate the pure deoxycholic acid.

In one embodiment, after the addition of nitrile at a temperature in the range of 40-90° C., the stirring is carried out for a period of 5-50 minutes, at a temperature in the range of 40-90° C. and the reaction mass is then cooled at a temperature in the range of −20° C. to 20° C. to precipitate the pure deoxycholic acid.

In one embodiment, the volume by volume ratio of nitrile solvent to ether is in the range of 15:1 to 1:1.

In one embodiment, the volume by volume ratio of nitrile solvent to ether is in the range of 9:1 to 2:1.

In one embodiment, cooling may be carried out at a temperature in the range of −20° C. to 20° C.

In one embodiment, present invention provides a process for deoxycholic acid, comprising the steps of:
a) dissolving the crude deoxycholic acid or salt thereof in tetrahydrofuran; and
b) isolating the pure deoxycholic acid or salt thereof by combining the solution obtained in (a) with acetonitrile followed by optional cooling.

In one embodiment, the addition of acetonitrile may be carried out at a temperature in the range of 40-90° C. and the reaction mass is then cooled to precipitate the pure deoxycholic acid.

The term "pure deoxycholic acid" refers to deoxycholic acid with a purity of at least about 99% as determined by HPLC In one embodiment, the term "pure deoxycholic acid" refers to deoxycholic acid with a purity of at least about 99% w/w as determined by HPLC and wherein the level of one or more impurities of compounds of formula II, A or $C_1$-$C_4$ alkyl ester thereof, B, C is less than 0.15% w/w as determined by HPLC

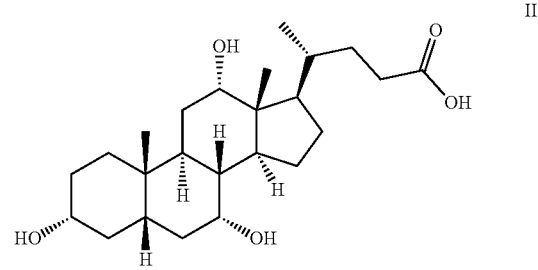

II

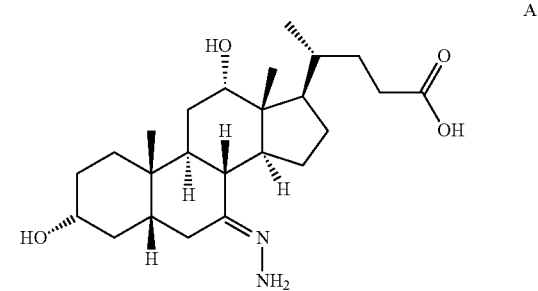

A

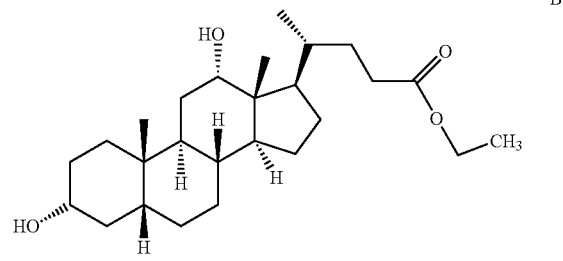

B

-continued

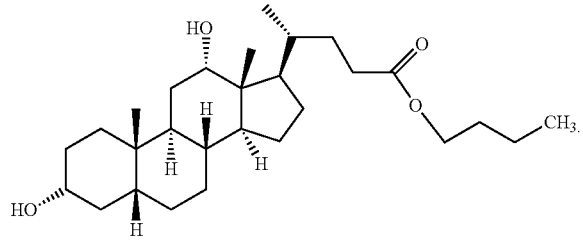

C

In one embodiment, present invention provides a process for deoxycholic acid or salt thereof, comprising the steps of:
a) dissolving the crude deoxycholic acid or salt thereof in tetrahydrofuran; and
b) isolating the pure deoxycholic acid or salt thereof by combining the solution obtained in (a) with acetonitrile followed by optional cooling to obtain deoxycholic acid with a purity of about 99% w/w as determined by HPLC and wherein the level of one or more impurities of compounds of formula II, A or $C_1$-$C_4$ alkyl ester thereof, B, C is less than 0.15% w/w as determined by HPLC.

In one embodiment, the acetonitrile is added at a temperature in the range of 50-65° C.

In one embodiment, the ratio of tetrahydrofuran:acetonitrile used is 1 volume: 1.5-10 volumes.

The pure deoxycholic acid thus obtained is isolated from the reaction mixture by any method known in the art. The method, may involve any of techniques, known in the art, including filtration by gravity or by suction, centrifugation, and the like, complete evaporation in, for example, a rotavapor, a vacuum paddle dryer or in a conventional reactor under vacuum, or concentrating the solution, cooling the solution if required and filtering the obtained solid by gravity or by suction, centrifugation, and the like.

In one embodiment, the pure deoxycholic acid obtained may be subjected to recrystallization in a solvent system selected from alcohol, ketones, water and mixtures thereof.

In one embodiment, the pure deoxycholic acid obtained may be subjected to recrystallization in a solvent system selected from ketones, water and mixtures thereof.

In one embodiment, the present invention provides a process for purifying deoxycholic acid, by dissolving deoxycholic acid in water and acetone, followed by optional charocoalization and adding water to the above mixture to precipitate deoxycholic acid.

In one embodiment, the present invention provides a process for purifying deoxycholic acid, by dissolving deoxycholic acid in water and acetone, followed by optional charocoalization and adding water to the above mixture and partially distilling out the water and acetone followed by optional addition of water to precipitate deoxycholic acid.

In one embodiment, the pure deoxycholic acid obtained may be subjected to recrystallization in a solvent system selected from acetone water mixture to obtain pure deoxycholic acid, with a purity of about 99% as determined by HPLC and wherein the level of one or more impurities of compounds of formula II, A, B, C is less than 0.15% w/w as determined by HPLC and is free from any organic volatile impurities and residual solvents.

In one embodiment, present invention provides a process for deoxycholic acid or salt thereof, comprising the steps of:
a) dissolving the crude deoxycholic acid or salt thereof in tetrahydrofuran;

b) isolating the pure deoxycholic acid or salt thereof by combining the solution obtained in (a) with acetonitrile followed by optional cooling to obtain deoxycholic acid with a purity of about 99% as determined by HPLC and wherein the level of one or more impurities of compounds of formula II, A, B, C is less than 0.15% w/w as determined by HPLC; and
c) subjecting the pure deoxycholic acid to recrystallization in a solvent system selected from acetone water mixture to obtain pure deoxycholic acid free from any organic volatile impurities and residual solvents.

The term "free from any organic volatile impurities" and "residual solvents" means the pure deoxycholic acid does not have any organic volatile impurities and residual solvents when determined by HPLC and GC methods.

In one embodiment the pure deoxycholic acid is free of acetonitrile and tetrahydrofuran.

The isolated deoxycholic acid may be dried in an oven, air tray dryer, vacuum tray dryer, rotary dryer, rotary vacuum dryer, flash dryer, spin flash dryer, fluid bed dryer, and the like.

In one embodiment, the present invention provides a process for the preparation of deoxycholic acid or salt thereof, a compound of formula I, Formula I

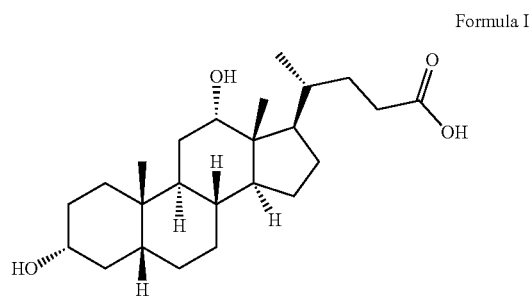

the process comprising the steps of:
a) reacting cholic acid, a compound of formula II with methanol to give a compound of formula III;

Formula II

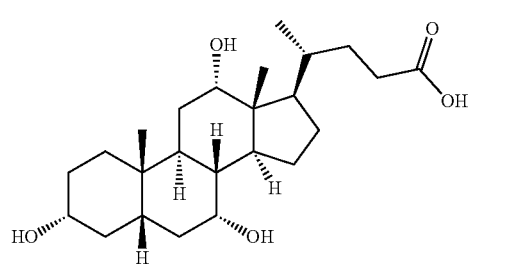

Formula III

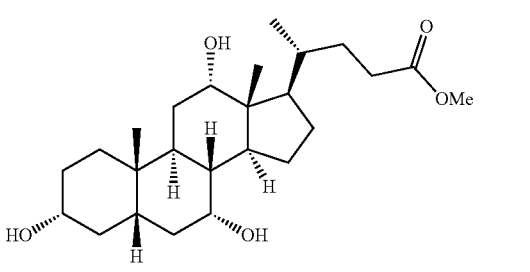

b) oxidizing the compound of formula III with alkali metal bromate, optionally in the presence of an alkali metal halide to obtain a compound of formula IV; and

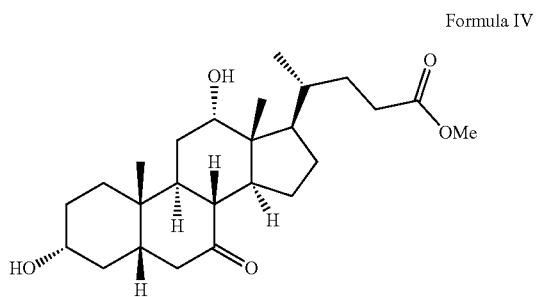

Formula IV c) reacting the compound of formula IV with hydrazine or hydrate thereof to obtain deoxycholic acid or salt thereof.

In one embodiment, in step a, cholic acid used is obtained from animal origin.

In one embodiment, in step a, cholic acid used is obtained from bovine and ovine bile.

In one embodiment, the cholic acid is obtained by treating ovine and bovine bile by alkaline hydrolysis at high temperatures. The alkaline hydrolysis may be carried out using sodium hydroxide, potassium hydroxide, sodium carbonate, potassium carbonate and the like.

In one embodiment, the temperature used for alkaline hydrolysis maybe in the range of 100-150° C.

In one embodiment, the level of chenodeoxycholic acid and cholic acid methyl ester in the cholic acid obtained is less than 0.5% w/w.

In one embodiment, in step a, cholic acid compound of formula II is reacted with methanol in presence of acid catalyst to obtain a compound of formula III.

The acid catalyst may be selected from the group consisting of sulphuric acid, hydrochloric acid, nitric acid and the like.

In one embodiment, in step a, cholic acid compound of formula II is reacted with thionyl chloride followed by reacting with methanol to obtain a compound of formula III.

In step b, the compound of formula III is oxidized with alkali metal bromate, optionally in the presence of an alkali metal halide to obtain a compound of formula IV.

In one embodiment, in step (b), the alkali metal bromate is selected from the group consisting of sodium bromate, potassium bromate, and mixtures thereof.

In one embodiment, in step (b) the alkali metal halide is selected from the group consisting of alkali metal iodide, alkali metal chloride, alkali metal bromide like sodium bromide, potassium bromide, and mixtures thereof.

In one embodiment, in step (b), the oxidation is carried out in an acidic environment.

In one embodiment, in step (b), the oxidation is carried out by using a mixture of sodium bromate, sodium bromide and acid.

In one embodiment, the acid is selected from sulphuric acid, p-toluene sulphonic acid, dry hydrogen chloride.

In one embodiment, the step (b) is carried out in a solvent selected from halogenated hydrocarbons, alcohols, or mixtures thereof.

The halogenated hydrocarbon may be selected from methylene dichloride, ethylene dichloride and the like The alcoholic solvent may be selected from methanol, ethanol, isopropanol, propanol, n-butanol, isobutanol and the like.

In one embodiment, the addition of sodium bromate is carried out in the temperature range of 0-15° C.

In one embodiment, after completion of reaction, the reaction mass is quenched in aqueous sodium metabisulfite solution and the organic layer containing the compound of formula IV is separated and subjected to distillation to isolate the compound of formula IV.

In one embodiment, the compound of formula IV is subjected to one or more recrystallizations in an organic solvent so as to remove residual water in compound of formula IV.

The organic solvent may be selected from the group consisting of acetates, ethyl acetate, isopropyl acetate, non-polar solvents like toluene, xylenes.

In one embodiment, the compound of formula IV is subjected to one or more recrystallizations in ethyl acetate, so as to obtain compound of formula IV with residual water content of not more than 1%.

In one embodiment, the compound of formula IV is subjected to crystallization by dissolving the compound of formula IV in a solvent and adding an antisolvent.

The solvent may be selected from ethyl acetate, methylene chloride.

The antisolvent may be selected from hydrocarbons such as hexane, heptane, cyclohexane, toluene and the like.

In one embodiment, the compound of formula IV is subjected to crystallization by dissolving the compound of formula IV in ethyl acetate and adding cyclohexane to obtain compound of formula IV in a purity of at least 99%.

In one embodiment, the compound of formula IV is reacted with hydrazine or hydrate thereof to obtain deoxycholic acid or salt thereof In one embodiment, the reaction may be carried out in an organic solvent system.

In one embodiment, the reaction may be carried out in an aqueous solvent system.

The aqueous solvent system may be water that may be used singly or may include water in combination with water miscible organic solvent system.

The water miscible organic solvent system may be selected from alcohols, glycols, nitriles, ketones and the like.

The alcohols and nitriles may be selected from the group as discussed supra.

The glycol may be selected from ethylene glycol, propylene glycol, polyethylene glycol and the like.

In one embodiment, a high boiling water miscible organic solvent is selected for the reaction of compound of formula IV with hydrazine or hydrate thereof.

In one embodiment, the aqueous solvent system is water and ethylene glycol.

In one embodiment, the compound of formula IV is reacted with hydrazine or hydrate in presence of a base.

In one embodiment, the base used may be selected from the group consisting of alkali metal hydroxide, alkaline earth metal hydroxide, alkali metal carbonate, alkaline earth metal carbonates.

In one embodiment, the reaction of compound of formula IV with hydrazine or hydrate thereof is carried out in presence of an alkali metal hydroxide in a solvent system comprising water and ethylene glycol.

The reaction may be carried out at a temperature in the range of 100-130° C. for a period of about 1-5 hours and then the temperature of the reaction mass may be raised to 155-180° C. for a period of about 6-7 hours.

In one embodiment, the reaction proceeds via removal of water prior to the temperature being raised to 155-180° C.

In one embodiment, the compound of formula IV is reacted with hydrazine or hydrate thereof in presence of an alkali metal hydroxide to form alkali metal salt of deoxycholic acid.

In one embodiment, the compound of formula IV is reacted with hydrazine or hydrate thereof in presence of potassium hydroxide to form potassium salt of deoxycholic acid.

In one embodiment, the reaction mass of step (c), is worked up by quenching in water; followed by a workup process involving one or more of the following steps:
a) extracting the reaction mass with an organic solvent, distilling out the organic solvent followed by azeotropic removal of organic solvent to form deoxycholic acid or salt thereof;
b) adding an acid to the reaction mass to precipitate the deoxycholic acid.

In one embodiment, the reaction mass of step (c), is worked up by quenching in water; followed by a workup process involving one or more of the following steps:
a) extracting the reaction mass with n-butanol;
b) distilling out the n-butanol followed by addition of water;
c) azeotropically removing n butanol by distillation to form deoxycholic acid salt;
d) adding an acid the deoxycholic acid salt to obtain deoxycholic acid.

In one embodiment, the present invention provides a process for deoxycholic acid by a process comprising
a) reacting the compound of formula IV with hydrazine or hydrate thereof in presence of alkali metal hydroxide to obtain alkali metal salt of deoxycholic acid;
b) quenching the reaction mass containing the alkali metal salt of deoxycholic acid in water;
c) extracting the reaction mass of step b with a water immiscible alcoholic solvent.
d) isolating the alkali metal salt of deoxycholic acid from the water immiscible alcoholic solvent;
e) treating the alkali metal salt of deoxycholic acid with an acid to isolate deoxycholic acid.

In one embodiment, the present invention provides a process for deoxycholic acid via potassium deoxycholate.

In one embodiment, the present invention provides potassium deoxycholate.

In one embodiment, the present invention provides a process for preparing anhydrous deoxycholic acid by slurrying the deoxycholic acid in a hydrocarbon solvent.

The hydrocarbon solvent can be selected as discussed supra.

In one embodiment, the present invention provides a process for purifying deoxycholic acid by reacting deoxycholic acid with an appropriate organic or inorganic base to form base addition salt and converting the base addition salt of deoxycholic acid to deoxycholic acid by reacting with acid.

Appropriate base addition salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, N-methyl-D-glucamine, 2-amino-2-(hydroxymethyl)-1,3-propanediol, and salts with amino acids such as, for example, arginine, lysine and the like.

The present invention provides a process for the preparation of deoxycholic acid, a compound of formula I, the process comprising:
a) reacting cholic acid, a compound of formula II with methanol to give a compound of formula III;
b) oxidizing the compound of formula III with an oxidizing agent selected from the group consisting of sodium hypochlorite, m-chloroperbenzoic acid, pyridinium chlorochromate, oxalyl chloride with DMSO and triethyl amine, aluminium isopropoxide, 2-iodoxybenzoic acid and potassium chromate to obtain a compound of formula IV; and
c) reacting the compound of formula IV with semicarbazide hydrochloride to obtain deoxycholic acid.

In one embodiment, the present invention provides pharmaceutical compositions comprising deoxycholic acid or salt, solvate thereof obtained by the processes herein described, having a $D_{50}$ and $D_{90}$ particle size of less than about 150 microns, preferably less than about 100 microns, more preferably less than about 50 microns, still more preferably less than about 20 microns, still more preferably less than about 15 microns and most preferably less than about 10 microns. The particle size disclosed here can be obtained by, for example, any milling, grinding, micronizing or other particle size reduction method known in the art to bring the solid state deoxycholic acid or salt, solvate thereof into any of the foregoing desired particle size range.

In one embodiment, the present invention provides pharmaceutical compositions comprising deoxycholic acid or salt, solvate thereof obtained by the processes herein described, having a $D_{90}$ particle size of less than 20 microns.

In one embodiment, the present invention provides pharmaceutical compositions comprising deoxycholic acid or salt, solvate thereof obtained by the processes herein described, having a $D_{50}$ particle size of less than 10 microns.

In one embodiment, the present invention provides deoxycholic acid characterized by an X-ray powder diffraction (XRPD) spectrum having peak reflections at about 7.6, 9.9, 14.2, 15.2 and 16.5±0.2°.

In one embodiment, the present invention provides deoxycholic acid, wherein the bacterial endotoxin is less than 240 EU/g, as determined by bacterial endotoxin test of USP 29.

In one embodiment, the present invention provides deoxycholic acid, wherein the total aerobic microbial count does not exceed 100 cfu/g and the total combined yeasts and molds count does not exceed 10 cfu/g, as determined by microbial limit test of USP 29.

In one embodiment, the present invention provides compound of formula III, where in level of impurity compound of formula D, wherein R, X and Y are selected from —H or —OH; and Z is selected from the group consisting of —OH, —OCH$_3$, —NHCH$_2$COOCH$_3$ is less than 0.15% w/w as determined by HPLC.

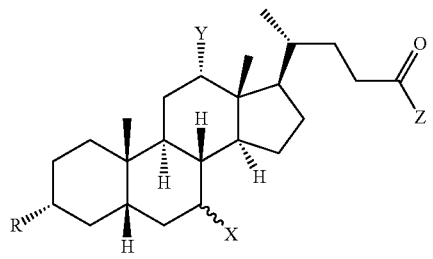

D

In one embodiment, the present invention provides compound of formula IV, wherein the level of impurity compound of formula D, wherein R is selected from the group consisting of —OH, =O; X and Y is selected from —H, —OH, =O; and Z is selected from group consisting of —OCH$_3$, —NHCH$_2$COOCH$_3$, —NHC$_2$H$_4$SO$_3$H is less than 0.15% w/w as determined by HPLC.

In one embodiment, the present invention provides compound of formula I, wherein level of impurities listed below is less than 0.15% w/w as determined by HPLC.

| Sr No | Chemical Name | Structure |
|---|---|---|
| 1 | 12α-hydroxy-5β-cholan-24-oic acid | 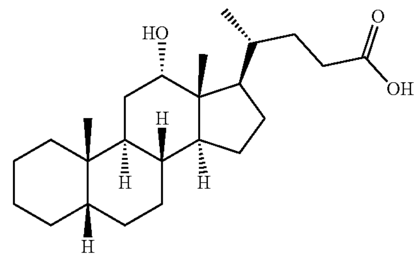 |
| 2 | 7α-,12α-dihydroxy5β-cholan-24-oic acid | 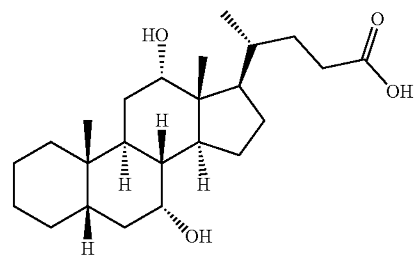 |
| 3 | Cholanic acid | 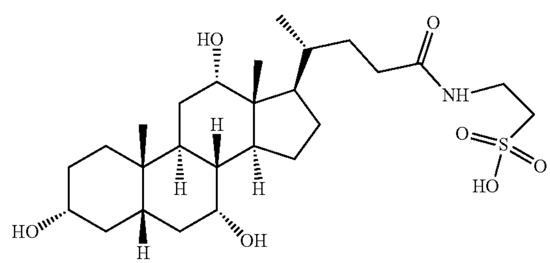 |
| 4 | Glycine,N-(3α,12α-dihydroxy-5β-cholan-24-oyl)-; Glycoallodeoxycholic acid | 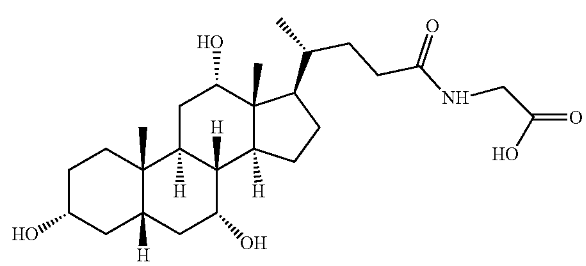 |
| 5 | Deoxycholic acid taurocholate | 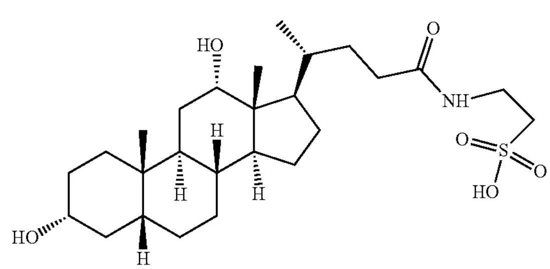 |

-continued
| Sr No | Chemical Name | Structure |
|---|---|---|
| 6 | Cholan-24-oic acid,3, 12-dihydroxy-, hydrazide,(3α,5β,12α)- | 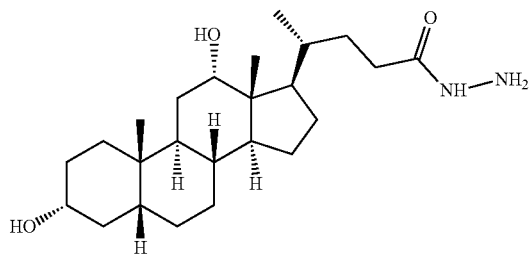 |
| 7 | Cholan-24-oic acid,7-hydrazono-3,12-dihydroxy-,(3α,5β,12α)-Methyl ester | 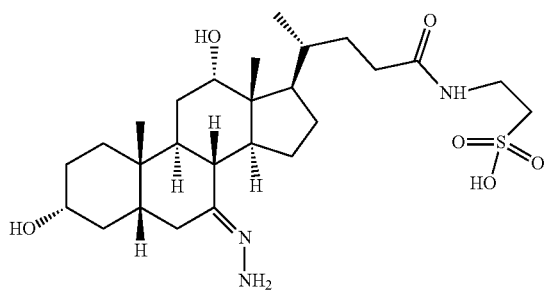 |
| 8 | Hydrazine hydrate | 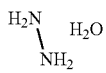 |
| 9 | Methyl 3α,12α-dihydroxy-7-oxo-5β-cholan-24-oate | 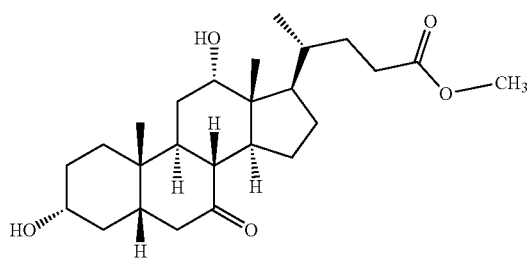 |
| 10 | Methyl 3α,12α-dihydroxy-5β-cholan-24-oate | 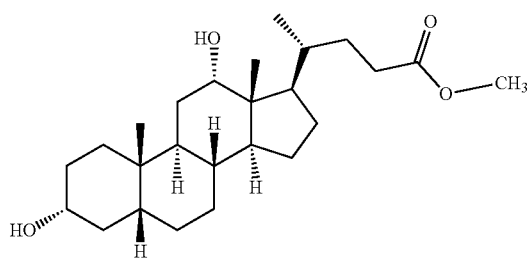 |
| 11 | 3α-Hydroxy-5β-cholan-24-oic acid | 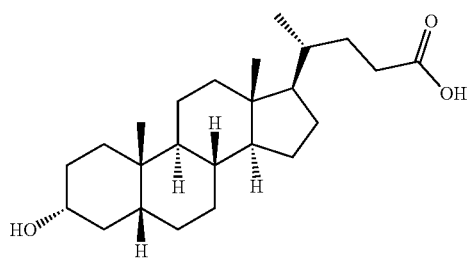 |

| Sr No | Chemical Name | Structure |
|---|---|---|
| 12 | 7-keto cholic acid | 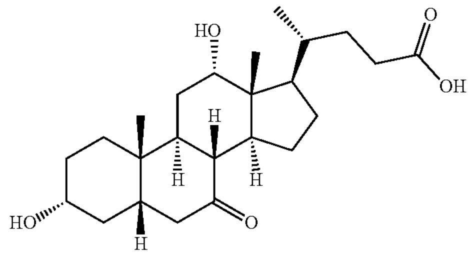 |
| 13 | 3α,7α-dihydroxy-5β-cholan-24-oic acid | 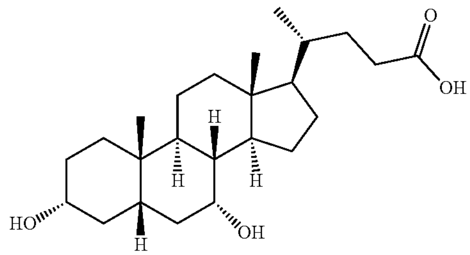 |

In one embodiment, the present invention provides compound of formula I, wherein level of 3α, 12β-dihydroxy-5β-cholan-24-oic acid, is less than 0.15% w/w as determined by HPLC.

The present invention provides deoxycholic acid obtained by above process, as analyzed for chemical purity using high performance liquid chromatography (HPLC) with the conditions described below.

Method I for Impurity II and Formula A or Ester Thereof:
Column: Eclipse plus C8 (150×4.6) mm, 3.5p. Mobile Phase: methanol: acetonitrile:water:glacial acetic acid (170: 300:530:0.6, V/V/V/V). Sample concentration of 20000 ppm was prepared in diluent containing methanol. Gradient elution was performed with a flow rate of 1.5 mL/min. The retention time of deoxycholic acid is about 30 minutes under these conditions.

Method II for Impurity B and C:
Column: Eclipse plus C8 (150×4.6) mm, 3.5μ. Mobile Phase: methanol: acetonitrile:water:glacial acetic acid (350: 350:300:0.6, V/V/V/V). Sample concentration of 20000 ppm was prepared in diluent containing methanol. Gradient elution was performed with a flow rate of 1.5 mL/min. The retention time of deoxycholic acid is about 5.3 minutes under these conditions.

The examples that follow are provided to enable one skilled in the art to practice the invention and are merely illustrative of the invention. The examples should not be read as limiting the scope of the invention as defined in the features and advantage.

EXAMPLES

Example 1: Preparation of Compound of Formula III

The cholic acid, compound of formula II (100 g) was added to methanol (1000 mL) at about room temperature. Sulfuric acid (18 g) was then added to the above reaction mixture and the reaction mass was maintained for about 5 h at room temperature. The reaction mass was then quenched with water and reaction mixture was stirred for about 30-40 min at about room temperature. The reaction mixture was filtered and the wet product obtained was slurry washed with water at room temperature. The slurry mass was then filtered and washed with water. The obtained wet solid was then dried at about 60'C to 65° C. to get cholic acid methyl ester having purity 98.9%; 5-β-cholanic acid methyl ester: not detected; compound of formula II: 0.79%

Example 2: Preparation of Compound of Formula IV 100 g of compound of formula III was dissolved in n-butanol (200 mL) and MDC (100 mL) solvent mixture and reaction mixture was cooled to about 7° C. to 12° C. To the above reaction mixture was then added sodium bromide (0.4 g), sulfuric acid and an aqueous sodium bromate (16 g). The reaction mass was maintained at about 7° C. to 12° C. for about 4 h and quenched by adding an aqueous sodium metabisulfite solution. The reaction mixture was stirred for about 15-25 min at room temperature and layers were separated. To the organic layer thus obtained water was added and again organic layer was separated. The organic layer was then distilled off completely under vacuum. Stripping of the obtained reaction mass was then carried out with ethyl acetate. To the reaction mass thus obtained was added ethyl acetate and the temperature of reaction mixture was then raised to about 70 to 80° C. and cyclohexane was then added to the reaction mixture. The reaction mass was then cooled to about room temperature and maintained for about 8 h and then filtered to obtain solid product; which was then suction dried and then further purified by ethyl acetate and cyclohexane solvent mixture to get compound IV (48 g) with purity 97.12%; 7-Keto methyl ester: 0.5%; 3,7,12-triketo cholic acid methyl ester: 0.19%; methyl-3-oxo-5β-cholan-24-oate: 0.39%; compound of formula III: 0.84%; compound of formula II: not detected.

Example 3: Preparation of Crude Deoxycholic Acid 100 g of compound IV was added to solvent mixture, containing aqueous potassium hydroxide (potassium hydroxide (279.6 g) and water) and ethylene glycol. This was followed by slow addition of hydrazine hydrate to the reaction mixture. The temperature of reaction mixture was then raised to about 120° C. to 125° C. and maintained at the same temperature for about 3 h and the water is distilled off slowly by reaction temperature to 135-155° C. The temperature of reaction mixture was then further raised to about 160° C. to 170° C. and maintained at the same temperature for about 6 h. The reaction mixture was then cooled to about 60° C. to 70° C. and water was then added to it. The reaction mixture was then cooled to about room temperature and n-butanol was then added to it. The product of the reaction was extracted in n-butanol. The n-butanol was then distilled off completely under vacuum to obtain a residue. This was followed by addition of water to the residue and distilling out the water and degassing to obtain a reaction mass. The reaction mass was dissolved in water and dilute sulfuric acid mixture and maintained at about room temperature for about 30-45 min. The precipitate obtained was filtered and washed with water; followed by slurry wash with water. The wet solid obtained was added to toluene and reaction mixture was heated to about 55° C. to 60° C. and stirred. The reaction mixture was then filtered and dried at about 50° C. to 60° C.

Purity: 85.49%; cholan-24-oic acid, 7-hydrazono-3,12-dihydroxy-, (3α,5β,12α)-methyl ester: 0.3%; 7-keto cholic acid: 1.35%; compound of formula II: 1.5%; compound of formula III: 2.2%; compound of formula A: 0.03%; compound of formula B: not detected; compound of formula C: 0.2%.

The dry solid was then dissolved in tetrahydrofuran and temperature was raised to about 60° C. to 70° C.; to this reaction mixture acetonitrile was added and stirred for about 10-15 min at same temperature. The reaction mixture was then cooled to about room temperature and maintained for about 10 h and then filtered. The solid product obtained was again purified by tetrahydrofuran and acetonitrile solvent mixture. The wet solid was then dried in vacuum oven.

Purity: 99.93%; cholan-24-oic acid, 7-hydrazono-3,12-dihydroxy-, (3α,5β,12α)-methyl ester: not detected; 7-Keto cholic acid: 0.03%; compound of formula II: 0.04%; compound of formula III: not detected by HPLC method I; compound of formula A or ester thereof: not detected by HPLC method I; compound of formula B and C: not detected by HPLC method II. XRPD 26 values for obtained compound are listed in the below table.

| Pos. [°2Th.] | Rel. Int. [%] |
|---|---|
| 7.25 | 12.09 |
| 7.42 | 9.72 |
| 7.85 | 2.16 |
| 9.01 | 3.40 |
| 9.88 | 21.43 |
| 10.37 | 3.65 |
| 11.78 | 1.25 |
| 12.53 | 1.66 |
| 12.94 | 2.04 |
| 13.56 | 6.27 |
| 14.03 | 100.00 |
| 14.55 | 10.04 |
| 15.01 | 7.73 |
| 15.49 | 4.63 |
| 16.40 | 19.04 |
| 17.12 | 7.09 |
| 17.68 | 10.68 |
| 17.98 | 12.29 |
| 18.39 | 5.77 |
| 19.90 | 3.99 |
| 20.79 | 5.49 |
| 21.90 | 7.13 |
| 22.46 | 10.41 |
| 23.13 | 4.69 |
| 24.12 | 4.68 |
| 24.93 | 0.66 |
| 26.04 | 2.23 |
| 26.56 | 3.21 |
| 27.46 | 1.91 |
| 28.37 | 1.34 |
| 29.66 | 1.23 |
| 31.32 | 0.80 |
| 32.01 | 0.57 |
| 33.25 | 0.39 |
| 35.68 | 1.86 |
| 36.55 | 2.36 |
| 38.87 | 0.95 |
| 41.09 | 0.94 |
| 42.41 | 0.78 |
| 44.05 | 0.56 |
| 45.46 | 0.59 |
| 46.80 | 0.70 |
| 47.92 | 0.46 |

The pure deoxycholic acid was then dissolved in acetone and water solvent mixture; the reaction mixture was then heated to about 55° C. to 60° C. and stirred for about 20-25 min at same temperature. To this reaction mixture charcoal was added and reaction mixture was stirred for about 45-60 min at the same temperature. The reaction mixture was then filtered and the filtrate thus obtained was cooled and water was added to it. This reaction mixture was maintained at about room temperature for 10 h and then filtered to obtained wet solid product. The wet product was then dried in vacuum oven.

Example 4: Purification of Deoxycholic Acid

The crude deoxycholic acid obtained from example 3 (100 g) was dissolved in acetone and water solvent mixture and the temperature of the reaction mixture was raised to about 50-60° C. To this reaction mixture charcoal was added and the reaction mixture was then stirred for about 60-70 min at the same temperature. The reaction mixture was then filtered and filtrate was distilled under vacuum to remove acetone. To the reaction mixture water was added and distilled out under vacuum. To the remaining reaction mixture, water was added and the mass was maintained at room temperature 2-3 hours and it was then filtered to obtain deoxycholic acid (90 g). The wet product was dried in vacuum oven.

OVI: acetone: 1067 ppm; THF: 46 ppm; toluene: 28 ppm; mesityl oxide: 2 ppm; ethylene glycol: not detected.

Purity: 99.95%, cholan-24-oic acid, 7-hydrazono-3,12-dihydroxy-, (3α,5β,12α)-methyl ester: not detected; 7-Keto cholic acid: not detected; compound of formula II: not detected; compound of formula III: not detected; compound of formula A, B and C: not detected. XRPD 20 values for obtained compound are listed in the below table

| Pos. [°2Th.] | Rel. Int. [%] |
|---|---|
| 7.55 | 47.95 |
| 8.95 | 0.67 |

-continued

| Pos. [°2Th.] | Rel. Int. [%] |
|---|---|
| 9.91 | 78.97 |
| 11.77 | 0.19 |
| 12.54 | 1.64 |
| 13.03 | 10.40 |
| 13.59 | 4.93 |
| 14.17 | 100.00 |
| 15.14 | 49.47 |
| 15.56 | 9.41 |
| 16.4 | 85.49 |
| 17.17 | 19.02 |
| 17.73 | 11.50 |
| 17.99 | 8.62 |
| 19.12 | 0.99 |
| 19.90 | 14.22 |
| 20.78 | 4.76 |
| 20.98 | 5.87 |
| 22.49 | 21.76 |
| 22.81 | 11.20 |
| 23.40 | 4.21 |
| 24.07 | 4.12 |
| 25.99 | 4.25 |
| 26.64 | 8.25 |
| 27.47 | 3.88 |
| 29.31 | 4.52 |
| 29.69 | 2.66 |
| 30.49 | 1.71 |
| 31.26 | 2.11 |
| 32.10 | 0.79 |
| 33.52 | 0.94 |
| 34.57 | 0.38 |
| 35.50 | 1.02 |
| 36.54 | 1.69 |
| 37.18 | 2.12 |
| 38.93 | 1.15 |
| 41.86 | 0.58 |
| 44.34 | 0.86 |
| 46.90 | 0.63 |
| 48.43 | 0.32 |

Example 5: Purification of Deoxycholic Acid

Crude Deoxycholic acid (90.0 gm) was added in tetrahydrofuran (300.0 mL) and temperature was raised to about 60° C. to 65° C.; to this reaction mixture acetonitrile (600 mL) was added and stirred for about 10-15 min at same temperature. The reaction mixture was then cooled to about room temperature and maintained for about 5 h and then filtered. The wet solid was then dried in vacuum oven to get Deoxycholic acid (52 gm). Purity: 99.95% w/w.

Example 6: Purification of Deoxycholic Acid

Crude Deoxycholic acid (104.0 gm) was added in tetrahydrofuran (312.0 mL) and temperature was raised to about 65° C. to 70° C.; to this reaction mixture acetonitrile (832 mL) was added and stirred for about 10-15 min at same temperature. The reaction mixture was then cooled to about room temperature and maintained for about 20 h and then filtered. The wet solid was then dried in vacuum oven to get Deoxycholic acid (82.6 gm). Purity: 99.90%.

Example 7: Purification of Deoxycholic Acid

Crude Deoxycholic acid (2.0 gm) was added in tetrahydrofuran (10.0 mL) and temperature was raised to about 60° C. to 65° C.; to this reaction mixture acetonitrile (50.0 mL) was added and then cooled to about room temperature and maintained for about 1.0 h and then filtered. The wet solid was then dried in vacuum oven to get Deoxycholic acid (0.66 gm).

The invention claimed is:

1. A process for the purification of deoxycholic acid of formula I or a salt thereof, comprising the steps of:

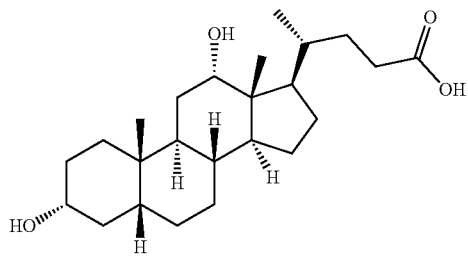

(a) dissolving crude deoxycholic acid or a salt thereof in an ether solvent; and
(b) isolating pure deoxycholic acid or a salt thereof by combining the solution obtained in step (a) with a nitrile solvent, followed by optional cooling, wherein the pure deoxycholic acid or salt thereof is obtained in a purity of at least 99% w/w and containing a level of less than 0.15% w/w as determined by HPLC of one or more impurities of a compound of formula II, a compound of formula A or a $C_1$-$C_4$ alkyl ester thereof, a compound of formula B, and a compound of formula C:

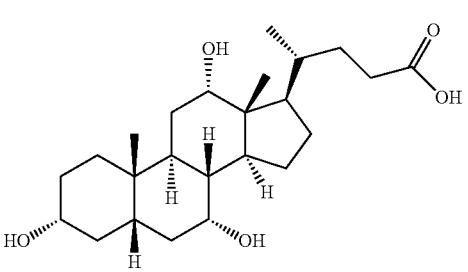

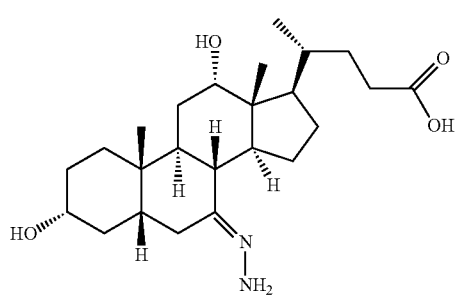

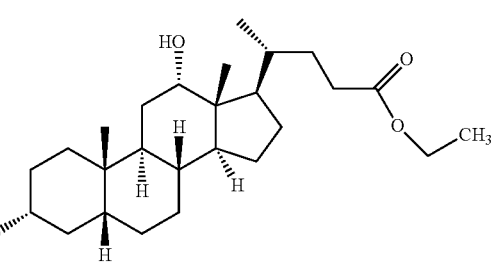

-continued

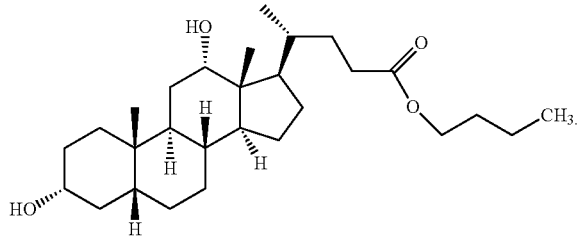

C

2. The process as claimed in claim 1, wherein in step (a), the ether solvent is selected from the group consisting of diethyl ether, methyl tertiary butyl ether, diisopropyl ether, tetrahydrofuran, dioxane, and mixtures thereof.

3. The process as claimed in claim 1, herein in step (b), the solution obtained in (a) is combined with the nitrile solvent at a temperature in the range of 40-90° C.

4. The process as claimed in claim 1, further comprising recrystallizing the pure deoxycholic acid or a salt thereof obtained in step (b) in a solvent system selected from the group consisting of an alcohol, a ketone, water and mixtures thereof.

5. The process as claimed in claim 4, wherein in step (b), the ketone solvent is acetone.

6. The process as claimed in claim 1, wherein the crude deoxycholic acid or salt thereof is prepared by a process comprising the steps of:
   (a) reacting cholic acid, a compound of formula II, with methanol to obtain a compound of formula III:

Formula II

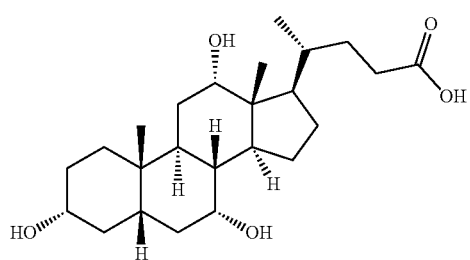

Formula III

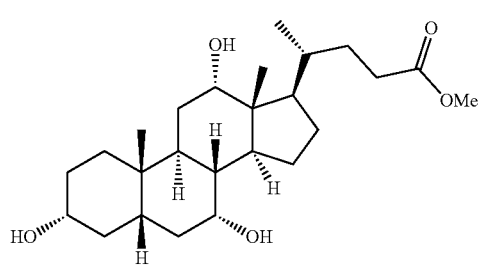

(b) oxidizing the compound of formula III with an alkali metal bromate, optionally in the presence of an alkali metal halide, to obtain a compound of formula IV; and Formula IV

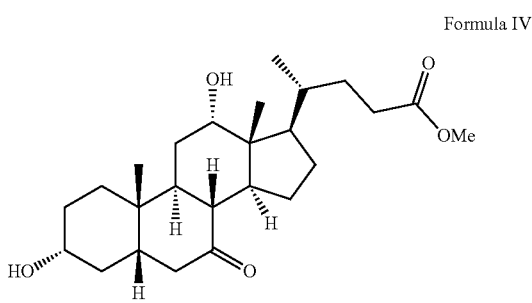

(c) reacting the compound of formula IV with hydrazine or a hydrate thereof to obtain deoxycholic acid or salt thereof.

7. The process as claimed in claim 6, wherein in step (b), the alkali metal bromate is selected from the group consisting of sodium bromate, potassium bromate, and mixtures thereof.

8. The process as claimed in claim 6, wherein in step (b), the alkali metal halide is selected from the group consisting of sodium bromide, potassium bromide and mixtures thereof.

9. The process as claimed in claim 6, wherein in step (c), the reaction is carried out in an aqueous solvent system.

10. The process as claimed in claim 9, wherein the aqueous solvent system is water and ethylene glycol.

11. The process as claimed in claim 9, wherein in step (c), the reaction is carried out in the presence of a base.

12. The process as claimed in claim 11, wherein the base is selected from the group consisting of an alkali metal hydroxide, an alkaline metal hydroxide, an alkali metal carbonate, and an alkaline earth metal carbonate.

13. The process as claimed in claim 12, wherein a deoxycholic acid salt with the alkali metal or alkaline earth metal are obtained.

14. The process as claimed in claim 6, wherein the reaction mass of step (c) is worked up by quenching in water; followed by a workup process involving one or more of the following steps:
   a) extracting the reaction mass with an organic solvent, distilling out the organic solvent followed by azeotropic removal of the organic solvent to form deoxycholic acid or salt thereof; and
   b) adding an acid to the reaction mass to precipitate the deoxycholic acid.

15. The process as claimed in claim 14, wherein the deoxycholic acid obtained is slurried in a hydrocarbon solvent.

* * * * *